US00PP32108P2

(12) United States Plant Patent
DeVries

(10) Patent No.: US PP32,108 P2
(45) Date of Patent: Aug. 25, 2020

(54) ROSE PLANT NAMED 'L6'

(50) Latin Name: ***Rosa* sp.**
Varietal Denomination: L6

(71) Applicant: Leendert DeVries, Arcata, CA (US)

(72) Inventor: Leendert DeVries, Arcata, CA (US)

(73) Assignee: Humboldt Land Company, LLC, Arcata, CA (US)

( * ) Notice: Subject to any disclaimer, the term of this patent is extended or adjusted under 35 U.S.C. 154(b) by 0 days.

(21) Appl. No.: 16/602,683

(22) Filed: Nov. 19, 2019

(51) Int. Cl.
*A01H 6/74* (2018.01)
*A01H 5/02* (2018.01)

(52) U.S. Cl.
USPC ..... Plt./107

(58) Field of Classification Search
USPC ..... Plt./107
CPC ..... A01H 6/74; A01H 5/02
See application file for complete search history.

*Primary Examiner* — Annette H Para
(74) *Attorney, Agent, or Firm* — Samuel R. McCoy, Jr.

(57) ABSTRACT

'L6' is a new and distinct *Rosa* sp. plant which is characterized by the combination of an upright growth habit with an abundance of long main stems, mid pink flowers born on terminal corymbs, an abundance of large vibrant red rose hips on each main stem, rose hips which remain very firm for an extended period of time relative to other cultivars, and the stability of these characteristics from generation to generation.

2 Drawing Sheets

Latin name of genus and species: The Latin name of the genus and species of the novel variety disclosed herein is *Rosa* sp.

Variety denomination: The inventive variety of *Rosa* sp. disclosed herein has been given the variety denomination 'L6'.

BACKGROUND OF THE INVENTION

Parentage: 'L6' is a seedling selection which resulted from the open pollination of *Rosa* 'Kolmade' (Community Plant Variety Rights grant number 29439, granted on Apr. 5, 2011), the seed parent, and *Rosa* 'Autumn Pride' (not patented), the pollen parent. In 2013, seeds were harvested from 'Kolmade' which resulted in approximately 3,200 seedlings. In July of 2014, the seedlings were transplanted into a field in Willow Creek, Calif. and grown to a mature size. From 2014 to 2016, these plants were evaluated for commercial production, based on criteria such as growth habit and fruiting habit. In September of 2016, one plant was observed which exhibited a large number of long main stems with relatively few prickles, a high density of large, very firm rose hips with a vibrant red color, and improved resistance to rust disease. After further evaluation and confirmation of the desirable traits first observed, the claimed plant was selected for commercialization in November of 2016 and given the breeder denomination, 'L6'.

Asexual Reproduction: Asexual propagation of 'L6', by way of softwood stem cuttings, was first performed in November of 2016 at the inventor's nursery in Willow Creek, Calif. Through three subsequent generations, the unique features of this cultivar have proven to be stable and true to type.

SUMMARY OF THE INVENTION

The following characteristics have been repeatedly observed and represent the distinguishing characteristics of the new *Rosa* cultivar 'L6'. These traits, in combination, distinguish 'L6' as a new and distinct cultivar.

1. 'L6' exhibits an upright growth habit with a relative abundance of long, upright main stems; and
2. 'L6' exhibits main stems with relatively few prickles and relatively minimal lateral branching; and
3. 'L6' exhibits an abundance of mid pink flowers with a single whorl of petals, born terminal corymbs; and
4. 'L6' exhibits an abundance of large, vibrant red rose hips born terminal corymbs, with a total of 25 to 40 rose hips on each main stem; and
5. 'L6' exhibits rose hips which remain very firm into late December in Willow Creek, Calif.; and
6. 'L6' exhibits improved resistance to rust (*Phragmidium* sp.).

DETAILED BOTANICAL DESCRIPTION

Figure 1:
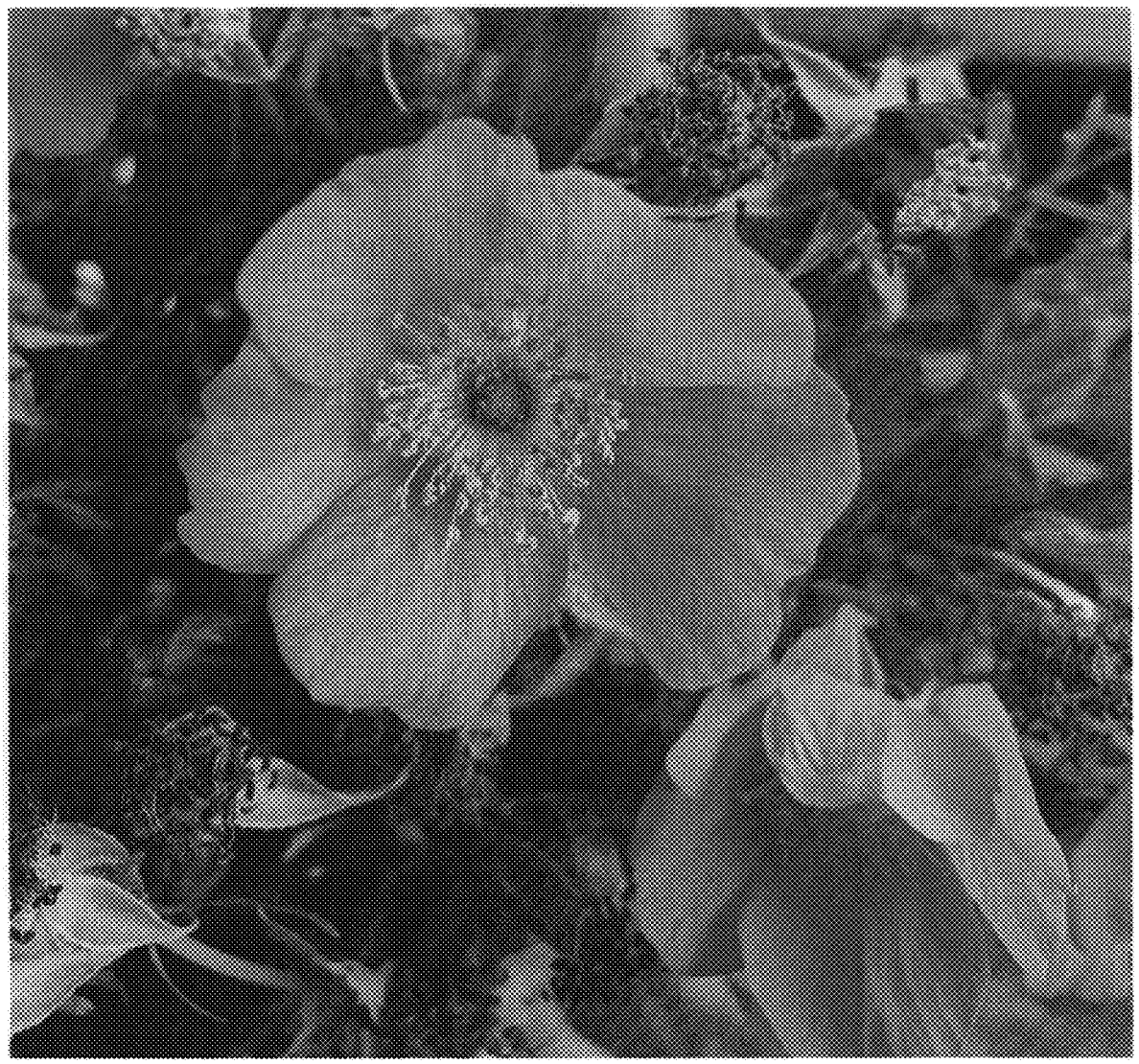
FIG. 1 illustrates, as nearly true as it is reasonably possible to make the same in color photographs of this type, the typical flower of 'L6'.
Figure 2:
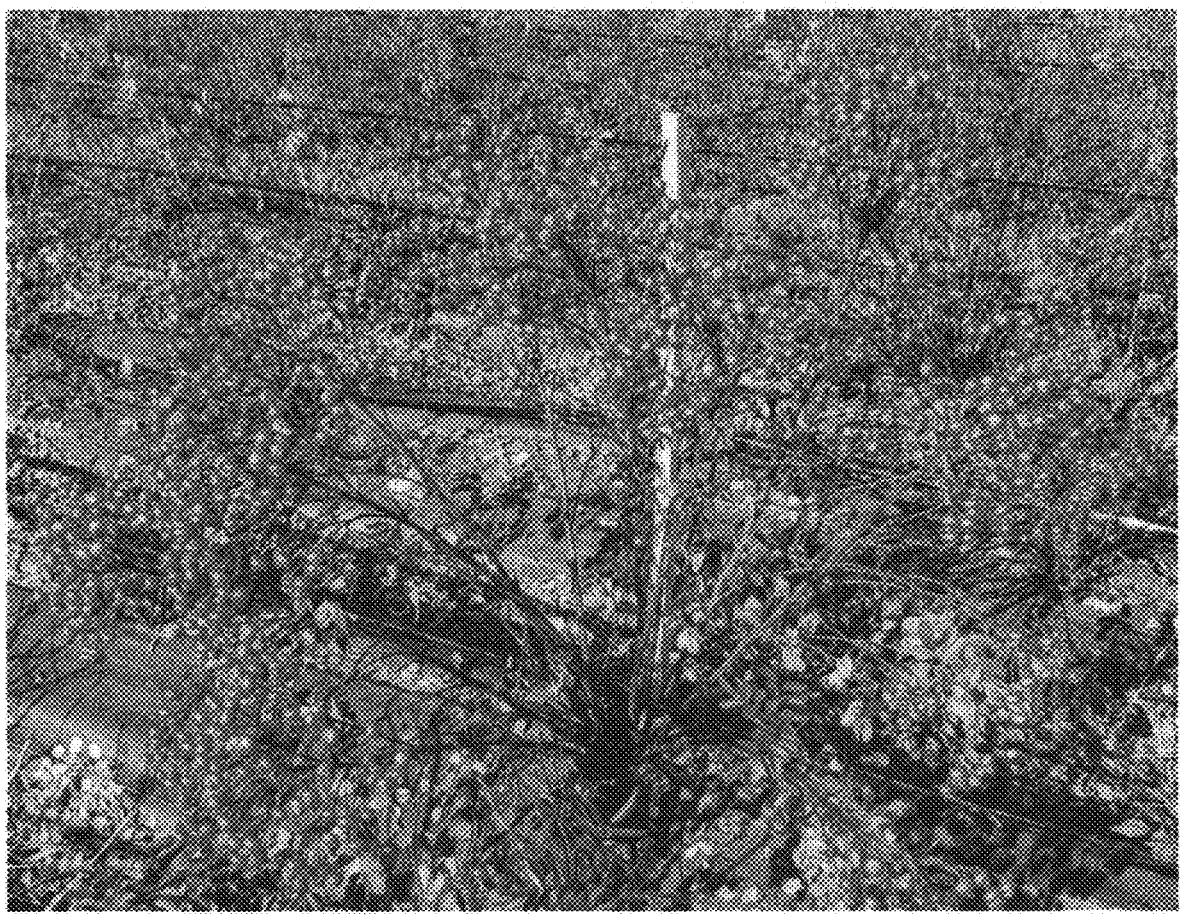
FIG. 2 illustrates, as nearly true as it is reasonably possible to make the same in color photographs of this type, the typical fruiting habit of 'L6'.

The following is a detailed botanical description of a new and distinct variety of a *Rosa* sp. known as 'L6'. Plant observations were made on field grown plants produced in Willow Creek, Calif. Unless indicated otherwise, the descriptions disclosed herein are based upon observations made of a mature 'L6' plant, transplanted into a loamy clay field in May of 2018 as a one year old rooted cutting grown in a 4 inch nursery pot. The plant received morning shade and were grown using conventional production techniques for this species. The plant was provided overhead irrigation for two months after transplant and thereafter received regular drip irrigation. Fertilizer was regularly applied using a fertigation technique, and the plant was occasionally treated for mites when required. In December of 2018, stems were harvested and the claimed plant was pruned to soil level. Plants have since been allowed to grow without further pruning. Observation data was recorded in the September of 2019.

Those skilled in the art will appreciate that certain characteristics will vary with older or, conversely, with younger plants. 'L6' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 1986 edition except where common terms of color are used.

A botanical description of 'L6' and comparisons with other varieties of *Rosa hybrida* are provided below.

General plant description:

*Growth rate*.—Vigorous.

*Growth habit*.—Upright deciduous shrub.

*Mature dimensions*.—Approximately 100 cm tall and 45 cm wide.

*Environmental tolerances*.—Hardy to USDA Hardiness Zone 5 through 9.

*Pest and disease susceptibility or resistance*.—Excellent resistance to rust disease (*Phragmidium* sp.). Otherwise, 'L6' is not any more or less tolerant or susceptible to pests or diseases known to effect *Rosa* sp.

*Propagation*.—Propagation is accomplished using softwood stem cuttings.

*Time to develop roots*.—Approximately 14 days with an average ambient temperature of 22 degrees Celsius.

*Crop time*.—Approximately 3 weeks are needed to produce a fully rooted cutting; after transplanting young plants grown in four inch nursery containers into a production field, fruit bearing stems can be harvested from the mature plants at the end of the second growing season.

Root system:

*Type*.—Moderately fibrous root system.

*Branching*.—Moderately branched.

*Density*.—Moderately dense.

*Distribution*.—Roots distributed evenly throughout the soil profile, from shallow to deep.

*Texture*.—Smooth; lacking root hairs.

*Color*.—Greyed-brown, nearest to in between RHS N199C and N199D.

Stems:

*Branching habit*.—Freely branching main stems give rise to a plurality of lateral branches.

*Quantity of mature main stems*.—Numerous; 14 main stems, as observed.

*General dimensions*.—Approximately 40 to 60 cm long; 0.5 cm in diameter near the base and tapering to 0.3 cm.

*Main stems*.—Length — Ranging from 70 to 90 cm. Diameter — Approximately 1.0 to 1.2 cm. Texture — Smooth; glabrous; prickles present. Color — Yellow-green, nearest to in between RHS 145B and 145C; becoming progressively suffused with greyed-orange, RHS 175A, with age. Prickles — Density — Sparse. Color — Nearest to yellow-green, RHS 145C, and heavily suffused with greyed-orange, RHS 165D, with age. Shape — Narrowly deltoid; recurved. Texture — Smooth.

*Lateral branches*.—Diameter — Average of 0.4 cm at the base. Texture — Smooth; glabrous; prickles present. Color — Yellow-green, nearest to in between RHS 145B and 145C; becoming progressively suffused with greyed-orange, RHS 175A, with age. Prickles — Density — Sparse. Color — Nearest to yellow-green, RHS 145B, and becoming progressively suffused with greyed-orange, RHS 175A, with age. Shape — Narrowly deltoid; recurved. Texture — Smooth.

Leaves:

*Arrangement*.—Imparipinnate compound leaves.

*Attachment*.—Petiolate.

*Dimensions*.—235 mm long and 190 mm wide.

*Abundance*.—Very abundant.

*Stipules*.—Size — 30 mm long and 4.5 mm wide. Stipule color, adaxial surface — Yellow-green, nearest to 147D. Stipule color, abaxial surface — Yellow-green, nearest to 147B. Stipitate glands — Only present at margins. Margins — Cilliate. Texture, adaxial surface — Glabrous; lightly bullate. Texture, abaxial surface — Glabrous; lightly bullate. Apex — Apiculate. Base — Winged.

*Petiole*.—Length — Average 25 mm. Diameter — Average 5.0 mm. Petiole color, adaxial surface — Yellow-green, nearest to in between RHS 144A and 144B. Petiole color, abaxial surface — Yellow-green, nearest to in between RHS 144A and 144B. Prickles — Absent. Stipitate glands — Absent. Texture, adaxial surface — Glabrous. Texture, abaxial surface — Papillate.

*Rachis*.—Length — Average 20 mm. Diameter — Average 2.0 mm. Color, adaxial surface — Yellow-green, nearest to in between RHS 144A and 144B, and suffused with greyed-red, RHS 178B. Color, abaxial surface — Yellow-green, nearest to RHS 145B. Stipitate glands — Absent. Texture, adaxial surface — Glabrous, with prickles. Texture, abaxial surface — Papillate. Prickles — Density — Sparse. Dimensions — 2.0 mm long and 1.5 mm wide. Color — Yellow-green, nearest to in between RHS 144A and 144B. Shape — Narrowly deltoid. Texture — Smooth.

*Leaflets*.—Quantity — Some leaves with 5 leaflets; others with 7 leaflets. Dimensions — Average size of the terminal leaflet is 37 mm long and 57 mm wide. Shape — Ovate. Apex — Acuminate. Base — Obtuse. Margins — Serrated; slight undulation is occasionally present. Texture, adaxial surface — Slightly to moderately rugose. Texture, abaxial surface — Slightly to moderately rugose. Luster, adaxial surface — Semi-glossy. Luster, abaxial surface — Matte. Color — Juvenile leaflet, adaxial surface — Yellow-green, RHS 144A, and margined greyed-red, RHS 178B. Juvenile leaflet, abaxial surface — Yellow-green, RHS 147C, and margined greyed-red, RHS 178B. Mature leaflet, adaxial surface — Yellow-green, nearest to RHS 147A. Mature leaflet, abaxial surface — Yellow-green, nearest to RHS 147A. Venation — Pattern — Reticulate. Color, adaxial surface — Yellow-green, nearest to in between RHS 144A and 144B. Color, abaxial surface — Yellow-green, nearest to RHS 145A. Petiolule — Dimensions — 15 mm long and 1.0 mm in diameter. Petiolule color, adaxial and abaxial surfaces — Yellow-green, RHS 144A. Prickles — Absent. Stipitate Glands — Absent. Texture, adaxial and abaxial surfaces — Smooth.

Inflorescence:

*Inflorescence type*.—Terminal corymbs, usually with 3 flowers; individual corymbs are tightly grouped together, giving the appearance of a single inflorescence with up to 17 flowers.

*Blooming habit*.—Blooms from June into July in Willow Creek, Calif.

*Quantity of flowers*.—Generally 3 flowers per corymb.

*Size*.—Corymbs are typically 110 mm tall and 70 to 80 mm wide.

*Peduncle*.—Surface — Lacking stipitate glands. Length — 50 mm. Diameter — 2.0 mm. Color — Yellow-green, nearest to in between RHS 144B and 144C. Strength — Strong. Texture — Glabrous; smooth.

Bud:

*Bud form*.—Pointed ovoid.

*Size*.—Upon opening, 10 to 13 mm in length and 6.0 to 8.0 mm diameter at its widest point.

*Texture*.—Smooth, glabrous, and moderately covered stipitate glands.

*Color, prior to bud-break*.—Yellow-green, nearest to a mixture of RHS 144A, 144B, and 146B.

Flower:

*Pedicel*.—Length — 35 to 40 mm. Diameter — 1.0 to 1.5 mm. Color — Yellow-green, nearest to in between RHS 144B and 144C. Strength — Moderately strong. Texture — Smooth; glabrous.

*Calyx*.—General — Comprised of five heavily-reflexed polysepalous sepals, with weak foliaceous appendages present on all sepals. Diameter of calyx — 45 mm, at anthesis. Sepals — Color, adaxial surface — Yellow-green, nearest to RHS 144A and 144B. Color, abaxial surface — Yellow-green, nearest to RHS 147C. Dimensions — Varying from 30 to 40 mm long and 5.0 mm wide at the base. Apex — Acute to acuminate. Base — Flat at union with receptacle. Texture, adaxial surface — Glabrous; smooth. Texture, abaxial surface — Slightly pubescent. Margins — Cilliate. Stipitate glands — Smooth, glabrous on the upper surface; moderately covered with stipitate glands on the lower surface.

*Corolla*.—General shape of corolla — Rounded. Shape of corolla when viewed from the side — Upon opening, upper portion — Flattened convex. Upon opening, lower portion — Concave. Open flower, upper portion — Flat. Open flower, lower portion — Concave. Aspect — Flowers held upright. Dimensions — When open, the average flower diameter is 90 mm and the average flower height is 50 mm. Fragrance — Light. Duration — On the plant 6 days. Senesced petals drop away cleanly. Petals — Petal arrangement — Single loose whorl of petals. Petal count — 5 petals. Petal reflex — Lightly reflexed. Petal margin — Entire; lightly undulated. Petal shape — Orbicular. Apex — Obtuse to slightly emarginate. Base — Obtuse. Dimensions — Approximately 20 mm long and 18 mm wide. Texture and luster, inner surface — Smooth; matte. Texture and luster, outer surface — Smooth; matte. Petal color, upon opening — Outer surface — Red-purple, nearest to RHS 72D. Inner surface — Red-purple, nearest to RHS 72C. Basal petal spots, upon opening — Dimensions — 3 mm high and 2 mm wide. Color, outer surface — Nearest to yellow, RHS 4D. Color, inner surface — Nearest to yellow, RHS 4D. Petal color, after opening — Outer surface — Nearest to a mixture of purple and purple-violet, RHS 78B and 80C. Inner surface — Nearest to a mixture of purple and purple-violet, RHS 78B and 80C. Basal petal spots, after opening — Dimensions — 3 mm high and 2 mm wide. Color, outer surface — Nearest to yellow, RHS 11D. Color, inner surface — Nearest to yellow, RHS 11D. Petal color, when fading — Outer surface — Nearest to a mixture of red-purple, RHS 70C, and purple-violet, RHS 80D. Inner surface — Nearest to in between red-purple, RHS 70D, and purple-violet, RHS 80D.

Reproductive organs:

*Stamens*.—Quantity — Approximately 100, on average, and regularly arranged around the styles. Anthers — Shape — Globose to oblong, with two anther sacs. Dimensions — 1.0 to 1.5 mm long and 0.75 to 1.0 mm wide. Color — Yellow-orange, RHS 20A. Pollen — Abundant. Pollen Color — Yellow, RHS 13A. Filaments — Color — Yellow-white, RHS 158D, and suffused with yellow at and near the base, nearest to RHS 6C. Length — 8 to 10 mm.

*Pistils*.—Quantity — Approximately 70; 67 observed. Overall length — 4.0 mm. Stigmas — Dimensions — 1 mm long and 1 mm in diameter. Position — Slightly inferior to anthers. Color — Nearest to a mixture of yellow, in between RHS 11A and 11B, and greyed-yellow, RHS 162A. Styles — Dimensions — 3.0 mm long and 0.75 mm in diameter. Color — Yellow, RHS 4D.

*Ovary*.—Dimensions — 5.0 mm long and 6.0 mm in diameter. Color — Green-white, RHS 157A.

*Receptacle*.—Shape — Pitcher-shaped. Dimensions — Approximately 6.0 mm high and 8.0 mm wide. Surface — Glabrous and slightly glaucous. Color — Yellow-green, nearest to a mixture of RHS 145A and 145B. Texture — Smooth.

Hips and seed formation:

*Hip*.—Shape — Ellipsoidal. Dimensions — 12 mm tall and 17 mm in diameter. Texture — Smooth. Luster — Glossy. Color, unripe — Yellow-green, nearest to in between RHS 144A and 144B. Color, ripe — Orange-red, nearest to a mixture of RHS 32A and 33A.

*Seed*.—Quantity — 62, as observed. Shape — Irregularly ovate. Dimensions — 4.0 mm long and 2 mm wide. Texture — Smooth. Luster — Slightly glossy. Color — Greyed-yellow, nearest to a combination of RHS 161A, 161B and 161C.

Comparisons with the Parents

Plants of the new cultivar 'L6' may be distinguished from its seed parent, *Rosa* sp. 'Kolmade' (Community Plant Variety Rights grant number 29439, granted on Apr. 5, 2011), by the characteristics described in Table 1.

TABLE 1

| Characteristic | 'L6' | 'Kolmade' |
|---|---|---|
| Plant height. | Grows to approximately 100 cm tall. | Grows to approximately 71 cm tall. |
| Development of main stems; plant productivity. | Main stem development is relatively prolific; producing 14 main stems on average, equating to a variety that is 45.8% more productive than 'Kolamade'. | Produces 9.6 main stems on average, equating to a variety that is 45.8% less productive than 'L6'. |
| Rose hip firmness. | Rose hips remain firm for up to 14 days longer than 'Kolamade', lasting into late December. | Rose hips begin to lose firmness (i.e. soften) by the second week of December in Willow Creek, California. |

Plants of the new cultivar 'L6' may be distinguished from its pollen parent, *Rosa* sp. 'Autumn Pride' (not patented), by the characteristics described in Table 2.

TABLE 2

| Characteristic | 'L6' | 'Autumn Pride' |
|---|---|---|
| Resistance to rust disease. | More resistant than 'Autumn Pride'. | Less resistant than 'L6'. |
| Development of main stems; plant productivity. | Main stem development is relatively prolific; producing 14 main stems, on average. | Produces 8.4 main stems, on average. |
| Rose hip firmness. | Rose hips remain firm for up to 30 days longer than 'Autumn Pride', lasting into late December. | Rose hips begin to lose firmness (i.e. soften) by the third week of November in Willow Creek, California. |

Comparison with the Closest Known Commercial Comparator

Plants of the new cultivar 'L6' may be distinguished from the most similar known commercial comparator, *Rosa* sp. 'Kolamaz' (U.S. Plant Pat. No. 13,582), by the characteristics described in Table 3.

TABLE 3

| Characteristic | 'L6' | 'Kolamaz' |
|---|---|---|
| Plant height. | Grows to approximately 100 cm tall. | Grows to approximately 74 cm tall. |
| Development of main stems; plant productivity. | Main stem development is relatively prolific; producing 14 main stems on average, equating to a variety that is 57.3% more productive than 'Kolamaz'. | Produces 8.9 main stems on average, equating to a variety that is 57.3% less productive than 'L6'. |
| Development of lateral branches. | Lateral branch development is minimal; approximately 86% less lateral branching than 'Kolamaz' which reduces the need for manual pruning or plant growth regulators to minimize lateral branching. | Lateral branch development is much greater, requiring manual pruning or the use of plant growth regulators to minimize lateral branching. |
| Rose hip firmness. | Rose hips remain firm for up to 40 days longer than 'Kolamaz', lasting into late December. | Rose hips begin to lose firmness (i.e. soften) by the second week of November in Willow Creek, California. |
| Abundance of rose hips. | Very abundant. | Not abundant. |
| Rose hip size. | Rose hips are approximately 16% larger than those of 'Kolamaz'. | Rose hips are approximately 16% larger than those of 'L6'. |

That which is claimed:

1. A new and distinct variety of rose plant named 'L6', as described and illustrated herein.

* * * * *